United States Patent
Litvak et al.

(10) Patent No.: US 9,687,650 B2
(45) Date of Patent: Jun. 27, 2017

(54) SYSTEMS AND METHODS FOR IDENTIFYING ONE OR MORE INTRACOCHLEAR DEAD REGIONS

(71) Applicant: ADVANCED BIONICS AG, Staefa (CH)

(72) Inventors: Leonid M. Litvak, Los Angeles, CA (US); Smita S. Agrawal, Stevenson Ranch, CA (US)

(73) Assignee: Advanced Bionics AG, Staefa (CH)

(*) Notice: Subject to any disclaimer, the term of this patent is extended or adjusted under 35 U.S.C. 154(b) by 0 days.

(21) Appl. No.: 15/024,022

(22) PCT Filed: Oct. 6, 2014

(86) PCT No.: PCT/US2014/059336
§ 371 (c)(1),
(2) Date: Mar. 22, 2016

(87) PCT Pub. No.: WO2015/054149
PCT Pub. Date: Apr. 16, 2015

(65) Prior Publication Data
US 2016/0243361 A1   Aug. 25, 2016

Related U.S. Application Data

(60) Provisional application No. 61/888,237, filed on Oct. 8, 2013.

(51) Int. Cl.
*A61N 1/00* (2006.01)
*A61N 1/36* (2006.01)
(Continued)

(52) U.S. Cl.
CPC .......... *A61N 1/36032* (2013.01); *A61B 5/125* (2013.01); *A61N 1/36014* (2013.01); *H04R 25/30* (2013.01); *H04R 25/505* (2013.01)

(58) Field of Classification Search
CPC ............ A61N 1/36032; A61N 1/36014; H04R 25/30; H04R 25/505
See application file for complete search history.

(56) References Cited

U.S. PATENT DOCUMENTS

2014/0371623 A1* 12/2014 Hong ................. A61B 5/04845
600/559

FOREIGN PATENT DOCUMENTS

WO   WO-2008/048383   4/2008

OTHER PUBLICATIONS

Moore, "Dead Regions in the Cochlea: Conceptual Foundations, Diagnosis, and Clinical Applications", *Ear & Hearing* 2004; 25; 98-116, (Apr. 2004), 98-116.

(Continued)

*Primary Examiner* — Robert N Wieland
(74) *Attorney, Agent, or Firm* — ALG Intellectual Property, LLC

(57) ABSTRACT

An exemplary system 1) presents, during a first time period, a tone in isolation to a patient by way of a receiver in communication with an ear of the patient, the tone having a predetermined frequency included in a frequency band, 2) presents, during a second time period, the tone together with a masking signal to the patient by way of the receiver, 3) uses an electrode located within an intracochlear region of the patient that is associated with the frequency band to record, during the first time period, a first evoked response that occurs in response to the presentation of the tone, and record, during the second time period, a second evoked response that occurs in response to the presentation of the tone together with the masking signal, and 4) determines, based on the first and second evoked responses, whether the intracochlear region is dead.

20 Claims, 14 Drawing Sheets

(51) Int. Cl.
*A61B 5/12* (2006.01)
*H04R 25/00* (2006.01)

(56) References Cited

OTHER PUBLICATIONS

International Search Report and Written Opinion received in International Application No. PCT/US14/059336, dated Feb. 16, 2015.
Markessis et al., *Frequency Tuning Curves Derived from Auditory Steady State Evoked Potentials: A Proof-of-Concept Study*; Ear and Hearing Feb. 2009; vol. 30, No. 1, ISSN: 1538-4667.
Moore et al., *A Test for the Diagnosis of Dead Regions in the Cochlea*; British Journal of Audiology; Whurr Publishers UK; vol. 34, No. 4, Aug. 2000; ISSN: 0300-5364.

\* cited by examiner

| US 9,687,650 B2 |
|---|

SYSTEMS AND METHODS FOR IDENTIFYING ONE OR MORE INTRACOCHLEAR DEAD REGIONS

RELATED APPLICATIONS

The present application claims priority to U.S. Provisional Patent Application No. 61/888,237, filed on Oct. 8, 2013, and entitled "Systems and Methods for Identifying One or More Intracochlear Dead Regions," the contents of which are hereby incorporated by reference in their entirety.

BACKGROUND INFORMATION

Many hearing loss patients have some degree of residual hearing in the low frequencies (e.g., below 1 kHz) and a severe hearing loss in the high frequencies (e.g., above 1 kHz). These people cannot benefit from traditional hearing aid amplification because of the severity of the hearing loss in the high frequencies. Nor are they classic cochlear implant candidates, because of their mostly intact low frequency residual hearing.

For this group of people, electro-acoustic stimulation ("EAS") systems have been developed that provide such patients with the ability to perceive both low and high frequencies. Electro-acoustic stimulation combines the functionality of a hearing aid and a cochlear implant together in the same ear by providing acoustic stimulation representative of low frequency audio content and electrical stimulation representative of high frequency content. The auditory nerve combines the acoustic and electric stimuli into one auditory signal. Results of various studies have shown that electro-acoustic stimulation may enhance speech understanding, pitch discrimination, and music appreciation.

Unfortunately, an EAS patient may have one or more regions in his or her cochlea that contain no (or very few) functioning inner hair cells (or simply "hair cells") and/or neurons. Such regions are referred to as "dead regions" and, if located at positions within the cochlea corresponding to the relatively low frequencies typically represented by acoustic stimulation, can impair the EAS patient's ability to perceive sounds represented by the acoustic simulation.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
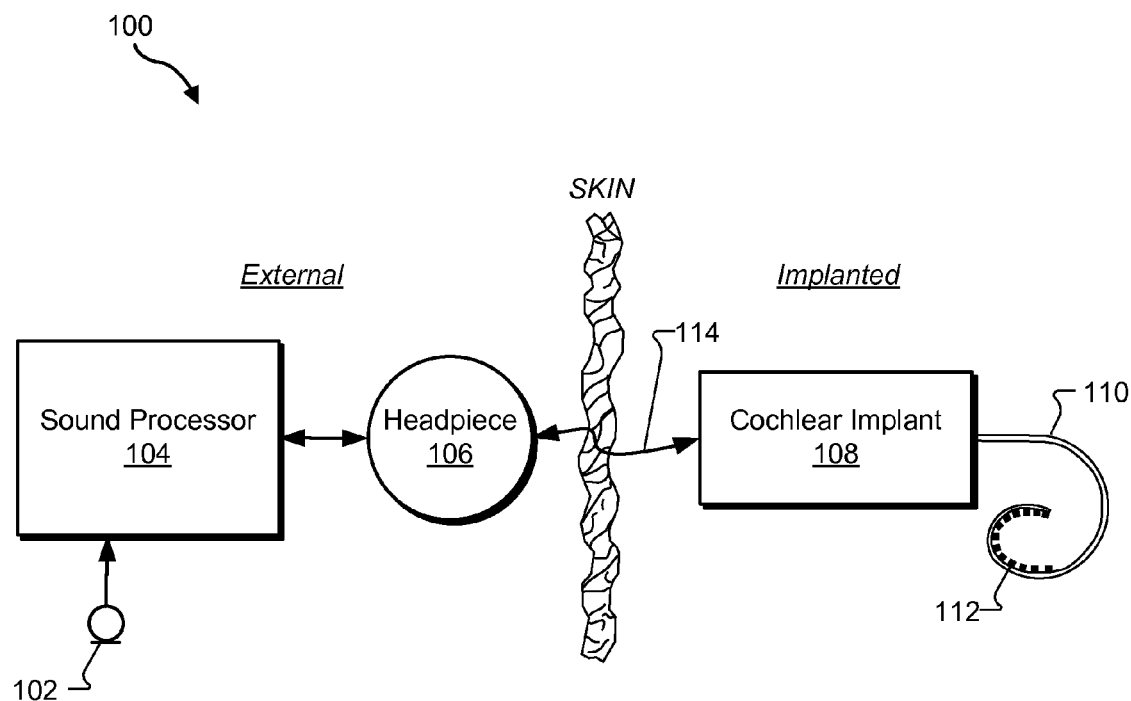
FIG. 1 illustrates an exemplary auditory prosthesis system according to described herein.

Systems and methods for identifying one or more intracochlear dead regions in an auditory prosthesis patient are described herein. For example, as will be described in more detail below, a diagnostic system may present, during a first time period, a tone in isolation to a patient by way of a receiver in communication with an ear of the patient, the tone having a predetermined frequency included in a frequency band. While the tone is being presented, the diagnostic system may use an electrode located within an intracochlear region of the patient that is associated with the frequency band to record a first evoked response that occurs in response to the presentation of the tone. The diagnostic system may then present, during a second time period and by way of the receiver, the same tone together with a masking signal that masks frequencies not included within the frequency band. While the tone and masking signal are being concurrently presented, the diagnostic system may use the same electrode to record a second evoked response that occurs in response to the presentation of the tone together with the masking signal. The diagnostic system may then determine, based on the first and second evoked responses, whether the intracochlear region is dead (i.e., whether the intracochlear region is a dead region).

To illustrate, the diagnostic system may compare the first and second evoked responses to determine whether the second evoked response is within a predetermined range of the first evoked response. If the second evoked response is within the predetermined range of the first evoked response (e.g., if the second evoked response is substantially the same as the first evoked response), the diagnostic system may determine that the intracochlear region is not a dead region (i.e., that the intracochlear region has functioning hair cells and/or neurons). However, if the second evoked response is not within the predetermined range of the first evoked response (e.g., if the second evoked response differs significantly from the first evoked response), the diagnostic system may determine that the intracochlear region is a dead region (i.e., that the intracochlear region does not have functioning hair cells and/or neurons). Physiological reasons for these determinations will be provided below.

Numerous advantages and benefits are associated with the systems and methods described herein. For example, by identifying a dead region within the cochlea of an auditory prosthesis patient, the diagnostic system may take one or more actions to compensate for the dead region and thereby provide an improved hearing experience for the patient. To illustrate, the diagnostic system may direct an EAS system associated with the patient to abstain from providing acoustic stimulation representative of acoustic content having frequencies associated with the dead region and instead provide electrical stimulation representative of such acoustic content. Another benefit of the systems and methods described herein is that one or more intracochlear dead regions may be identified without requiring verbal feedback from the patient. This may be especially beneficial in pediatric fittings and in other situations in which verbal feedback is unavailable. Other benefits and/or advantages provided by the disclosed systems and methods will be made apparent herein.

FIG. 1 illustrates an exemplary auditory prosthesis system 100. Auditory prosthesis system 100 may include a microphone 102, a sound processor 104, a headpiece 106 having a coil disposed therein, a cochlear implant 108, and an electrode array 110 (also referred to as a "lead") with a plurality of electrodes 112 disposed thereon. Additional or alternative components may be included within auditory prosthesis system 100 as may serve a particular implementation.

As shown, auditory prosthesis system 100 may include various components configured to be located external to a patient including, but not limited to, microphone 102, sound processor 104, and headpiece 106. Auditory prosthesis system 100 may further include various components configured to be implanted within the patient including, but not limited to, cochlear implant 108 and electrode array 110.

Microphone 102 may be configured to detect audio signals presented to the patient and output output signals representative of the audio signals for processing by sound processor 104. Microphone 102 may be implemented in any suitable manner. For example, microphone 102 may include a "T-Mic" or the like that is configured to be placed within the concha of the ear near the entrance to the ear canal. Such a microphone may be held within the concha of the ear near the entrance of the ear canal by a boom or stalk that is attached to an ear hook configured to be selectively attached to sound processor 104 (i.e., to a housing that houses sound processor 104). Additionally or alternatively, microphone 102 may be implemented by a microphone disposed within headpiece 106, a microphone disposed within a housing that houses sound processor 104, a microphone located in the ear canal, and/or any other suitable microphone as may serve a particular implementation.

Sound processor 104 (i.e., one or more components included within sound processor 104) may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, input by way of a CPI, etc.) to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. To this end, sound processor 104 may process the one or more audio signals in accordance with a selected sound processing strategy or program to generate appropriate stimulation parameters for controlling cochlear implant 108. Sound processor 104 may be housed within any suitable housing (e.g., a behind-the-ear ("BTE") unit, a body worn device, and/or any other sound processing unit as may serve a particular implementation).

In some examples, sound processor 104 may wirelessly transmit stimulation parameters (e.g., in the form of data words included in a forward telemetry sequence) and/or power signals to cochlear implant 108 by way of a wireless communication link 114 between headpiece 106 and cochlear implant 108. It will be understood that communication link 114 may include a bi-directional communication link and/or one or more dedicated uni-directional communication links.

Headpiece 106 may be communicatively coupled to sound processor 104 and may include an external antenna (e.g., a coil and/or one or more wireless communication components) configured to facilitate selective wireless coupling of sound processor 104 to cochlear implant 108. Headpiece 106 may additionally or alternatively be used to selectively and wirelessly couple any other external device to cochlear implant 108. To this end, headpiece 106 may be configured to be affixed to the patient's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transmitted between sound processor 104 and cochlear implant 108 via a communication link 114 (which may include a bi-directional communication link and/or one or more dedicated uni-directional communication links as may serve a particular implementation).

Cochlear implant 108 may include any type of implantable stimulator that may be used in association with the systems and methods described herein. For example, cochlear implant 108 may be implemented by an implantable cochlear stimulator. In some alternative implementations, cochlear implant 108 may include a brainstem implant and/or any other type of cochlear implant that may be implanted within a patient and configured to apply stimulation to one or more stimulation sites located along an auditory pathway of a patient.

In some examples, cochlear implant 108 may be configured to generate electrical stimulation representative of an audio signal processed by sound processor 104 (e.g., an audio signal detected by microphone 102) in accordance with one or more stimulation parameters transmitted thereto by sound processor 104. Cochlear implant 108 may be further configured to apply the electrical stimulation to one or more stimulation sites (e.g., one or more intracochlear regions) within the patient via one or more electrodes 112 disposed along electrode array 110. In some examples, cochlear implant 108 may include a plurality of independent current sources each associated with a channel defined by one or more of electrodes 112. In this manner, different stimulation current levels may be applied to multiple stimulation sites simultaneously by way of multiple electrodes 112.

Figure 2:
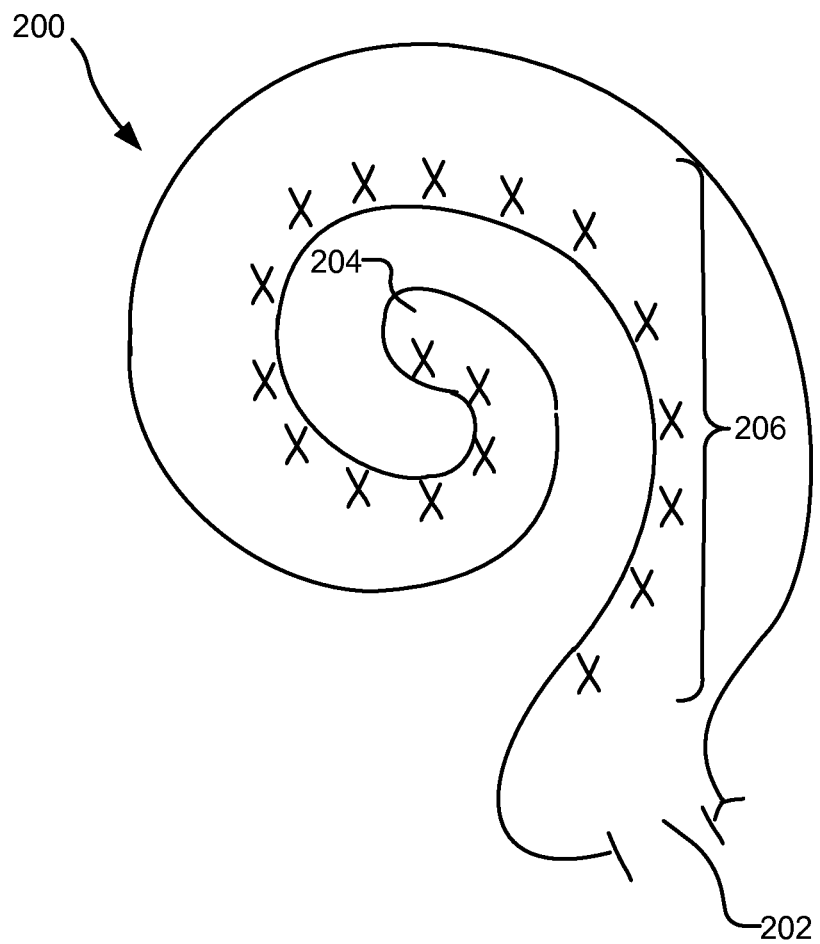
FIG. 2 illustrates a schematic structure of the human cochlea according to principles described herein.

FIG. 2 illustrates a schematic structure of the human cochlea 200 into which electrode array 110 may be inserted. As shown in FIG. 2, the cochlea 200 is in the shape of a spiral beginning at a base 202 and ending at an apex 204. Within the cochlea 200 resides auditory nerve tissue 206, which is denoted by Xs in FIG. 2. The auditory nerve tissue 206 is organized within the cochlea 200 in a tonotopic manner. Relatively low frequencies are encoded at or near the apex 204 of the cochlea 200 (referred to as an "apical region") while relatively high frequencies are encoded at or near the base 202 (referred to as a "basal region"). Hence, electrical stimulation applied by way of electrodes disposed within the apical region (i.e., "apical electrodes") may result in the patient perceiving relatively low frequencies and electrical stimulation applied by way of electrodes disposed within the basal region (i.e., "basal electrodes") may result in the patient perceiving relatively high frequencies. The delineation between the apical and basal electrodes on a particular electrode array may vary depending on the insertion depth of the electrode array, the anatomy of the patient's cochlea, and/or any other factor as may serve a particular implementation.

The auditory prosthesis system 100 illustrated in FIG. 1 may be referred to as a cochlear implant system because sound processor 104 is configured to direct cochlear implant 108 to generate and apply electrical stimulation representative of audio content (e.g., one or more audio signals) to one or more stimulation sites within the patient by way of one or more of electrodes 112.

Figure 3:
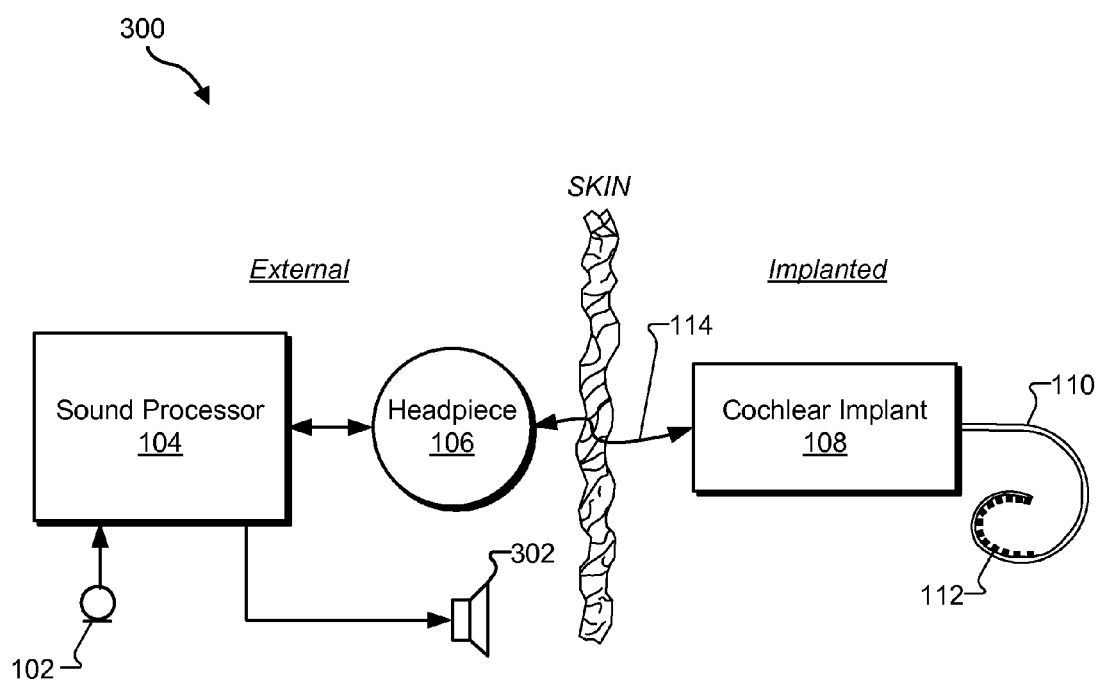
FIG. 3 illustrates an exemplary implementation of the auditory prosthesis system of FIG. 1 according to principles described herein.

FIG. 3 illustrates an exemplary implementation 300 of auditory prosthesis system 100 in which auditory prosthesis system 100 is further configured to provide acoustic stimulation to the patient. Hence, implementation 300 shown in FIG. 3 may be referred to as an EAS system.

As shown, implementation 300 may further include a receiver 302 (also referred to as a loudspeaker). Receiver 302 may be in communication with an ear of the patient (e.g., located at an entrance or within the ear canal of the patient). In this configuration, sound processor 104 (which, in implementation 300, may be referred to as an "EAS sound processor") may be configured to direct receiver 302 to apply acoustic stimulation representative of audio content included in relatively low frequency bands (e.g., below 1000 Hz) to the patient and cochlear implant 108 to apply electrical stimulation representative of audio content included in relatively high frequency bands (e.g., above 1000 Hz) to one or more stimulation sites within the patient by way of one or more of electrodes 112.

As mentioned, it may be desirable to identify one or more dead regions within a cochlea of an auditory prosthesis patient. For example, a patient may be fitted with a cochlear implant system, such as that illustrated in FIG. 1. In this scenario, it may be desirable to objectively determine whether the patient has one or more dead regions associated with the relatively low frequency bands in order to determine whether the patient is a candidate for an upgrade to an EAS system. The systems and methods may provide this objective determination. As another example, a patient may already be fitted with an EAS system, such as that illustrated in FIG. 3. In this scenario, it may be desirable to determine whether the patient has one or more dead regions in order to appropriately set one or more control parameters associated with the EAS system. The systems and methods may provide this determination as well.

Figure 4:
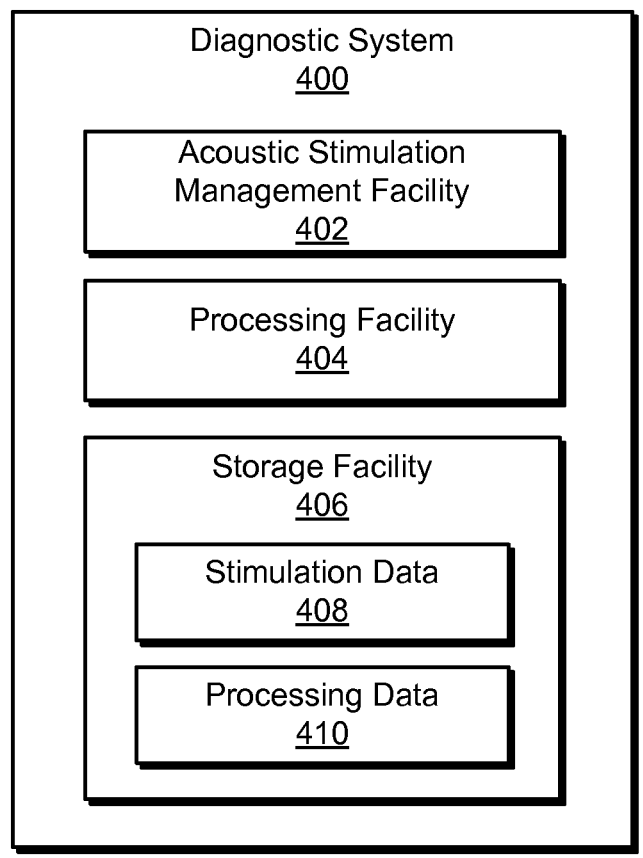
FIG. 4 illustrates an exemplary diagnostic system according to principles described herein.

FIG. 4 illustrates an exemplary diagnostic system 400 that may be configured to identify one or more intracochlear dead regions in an auditory prosthesis patient. As shown, diagnostic system 400 may include an acoustic stimulation management facility 402, a processing facility 404, and a storage facility 406, which may be in communication with one another using any suitable communication technologies. Storage facility 406 may be configured to maintain stimulation data 408 generated and/or used by acoustic stimulation management facility 402, and processing data 410 generated and/or used by processing facility 404. Storage facility 406 may maintain additional or alternative data as may serve a particular implementation. One or more of facilities 402-406 may include one or more computing devices and/or processors configured to perform one or more of the functions described herein.

Acoustic stimulation management facility 402 may be configured to present various types of acoustic stimulation to a patient. For example, acoustic stimulation management facility 402 may present one or more tones, one or more masking signals, and/or any other type of acoustic stimulation as may serve a particular implementation.

In order to determine whether a particular intracochlear region within a patient is dead, acoustic stimulation management facility 402 may present, during a first time period, a tone in isolation to the patient by way of a receiver in communication with an ear of the patient. The tone may have a predetermined frequency included in a frequency band associated with a particular electrode located within the cochlea of the patient.

Figure 5:
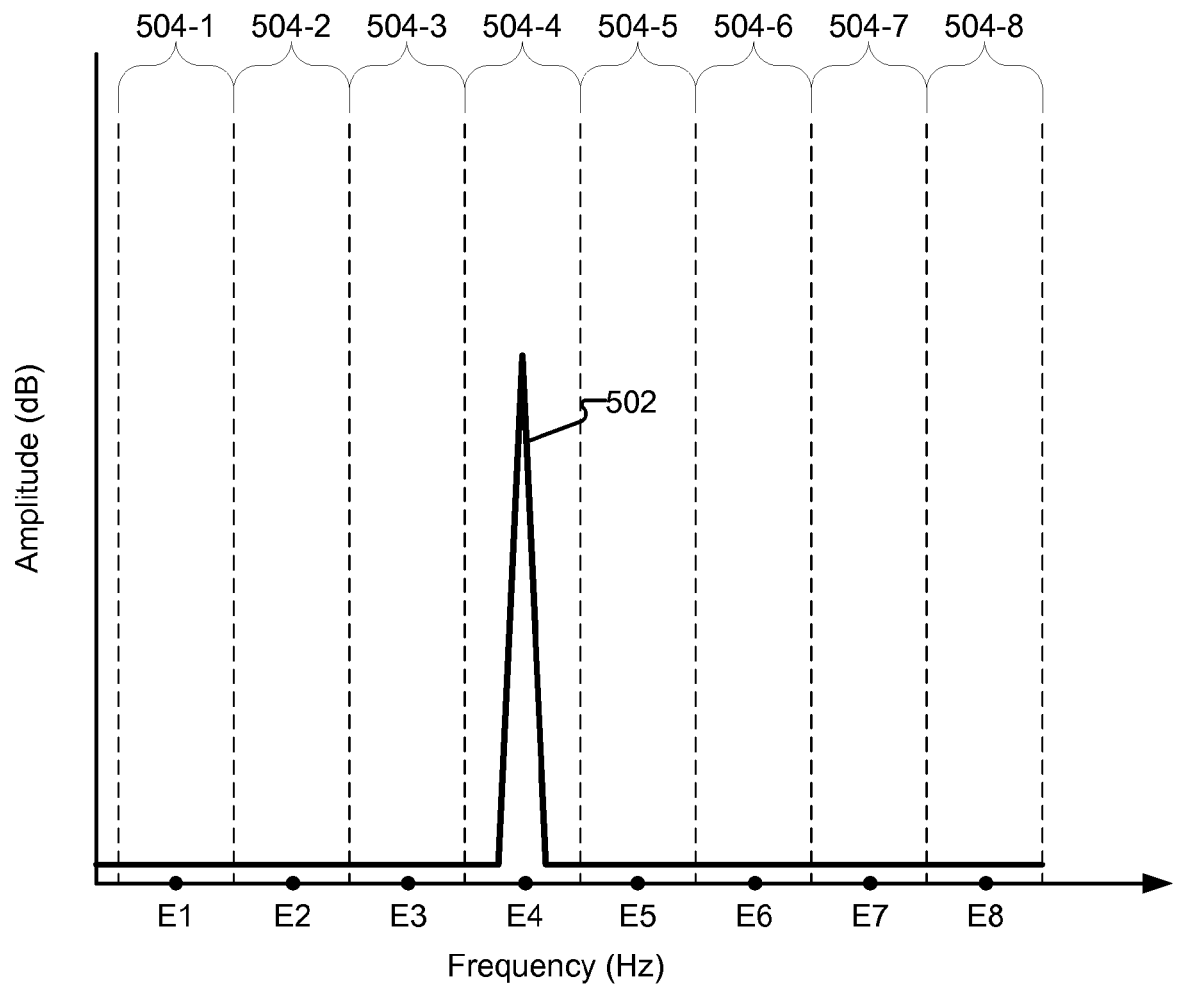
FIG. 5 shows an exemplary frequency domain representation of a tone that may be presented to an auditory prosthesis patient according to principles described herein.

To illustrate, FIG. 5 shows an exemplary frequency domain representation of a tone 502 that may be presented to an auditory prosthesis patient. As shown, a frequency spectrum may be divided into a plurality of frequency bands 504 (e.g., frequency bands 504-1 through 504-8). Each frequency band may be associated with a particular electrode included in a plurality of intracochlear electrodes E1 through E8. In other words, each electrode is located within an intracochlear region that corresponds to a particular frequency band. For example, electrode E1 is located within an intracochlear region that is associated with frequency band 504-1, electrode E2 is located within an intracochlear region that is associated with frequency band 504-2, etc. Eight electrodes and eight frequency bands 504 are shown in FIG. 5 for illustrative purposes only. It will be recognized that any other number of electrodes may be located within the cochlea and that the electrodes may be associated with any other number of frequency bands as may serve a particular implementation.

As shown in FIG. 5, tone 502 has a frequency located within frequency band 504-4, which is associated with electrode E4. Tone 502 may alternatively have any other frequency as may serve a particular implementation. As mentioned, tone 502 may be presented in isolation during a first time period. In other words, tone 502 is presented by itself (i.e., not in the presence of a masking signal) during the first time period. The first time period may be of any suitable duration as may serve a particular implementation.

As mentioned, acoustic stimulation management facility 402 may present the tone (e.g., tone 502) by way of a receiver in communication with an ear of the patient. This may be performed in any suitable manner. For example, acoustic stimulation management facility 402 may direct receiver 302 (or any other receiver in communication with the ear of the patient) to present the tone to the patient.

Returning to FIG. 4, processing facility 404 may be configured to perform various processing operations. For example, while the tone is being applied by acoustic stimulation management facility 402 during the first time period, processing facility 404 may use an electrode located within an intracochlear region of the patient that is associated with the frequency band that includes the frequency of the tone to monitor for and record a first evoked response that occurs in response to the presentation of the tone.

As used herein, an "evoked response" may include any type of cochlear response and/or neural response. Exemplary cochlear responses include, but are not limited to, cochlear microphonics, summating potentials, otoacoustic emissions, etc. Exemplary neural responses include, but are not limited to, auditory nerve responses, brainstem responses, compound action potentials, frequency following responses, etc. An evoked response may additionally or alternatively include any other type of response that may occur in response to application of a tone or any other type of acoustic stimulation.

Figure 6:
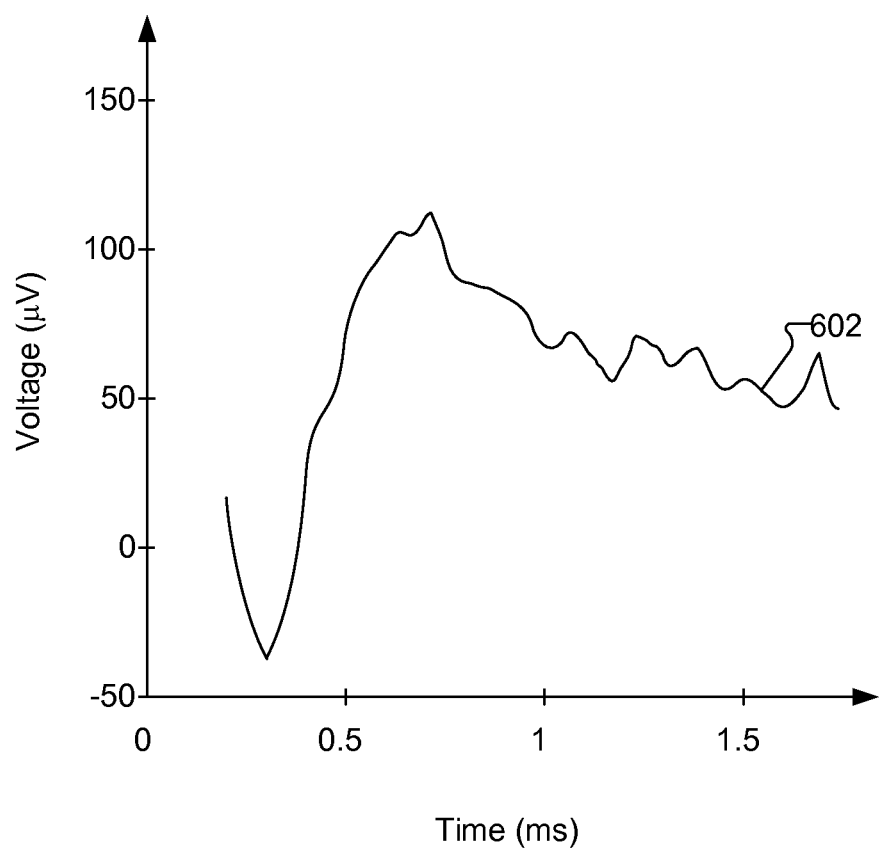
FIG. 6 illustrates an exemplary evoked response according to principles described herein.

FIG. 6 illustrates an exemplary evoked response 602 that may occur in response to a presentation of tone 502 in isolation. As mentioned, tone 502 has a frequency included within frequency band 504-4. Hence, processing facility 404 may use electrode E4, which, as shown in FIG. 5, is located in an intracochlear region associated with frequency band 504-4, to record evoked response 602. This may be done in any suitable manner. For example, processing facility 404 may direct cochlear implant 108 to use electrode E4 to record evoked response 602 and then transmit data representative of the evoked response 602 to processing facility 404 for analysis.

After the first evoked response (e.g., evoked response 602) has been recorded, acoustic stimulation management facility 402 may present, during a second time period that does not overlap with the first time period, the same tone together with a masking signal to the patient by way of the receiver. It will be recognized that the order in which the tone and then the tone and masking signal are presented may be varied as may serve a particular implementation. For example, the second time period may be subsequent to or proceed the first time period as may serve a particular implementation. The second time period may be of any suitable duration.

Figure 7:
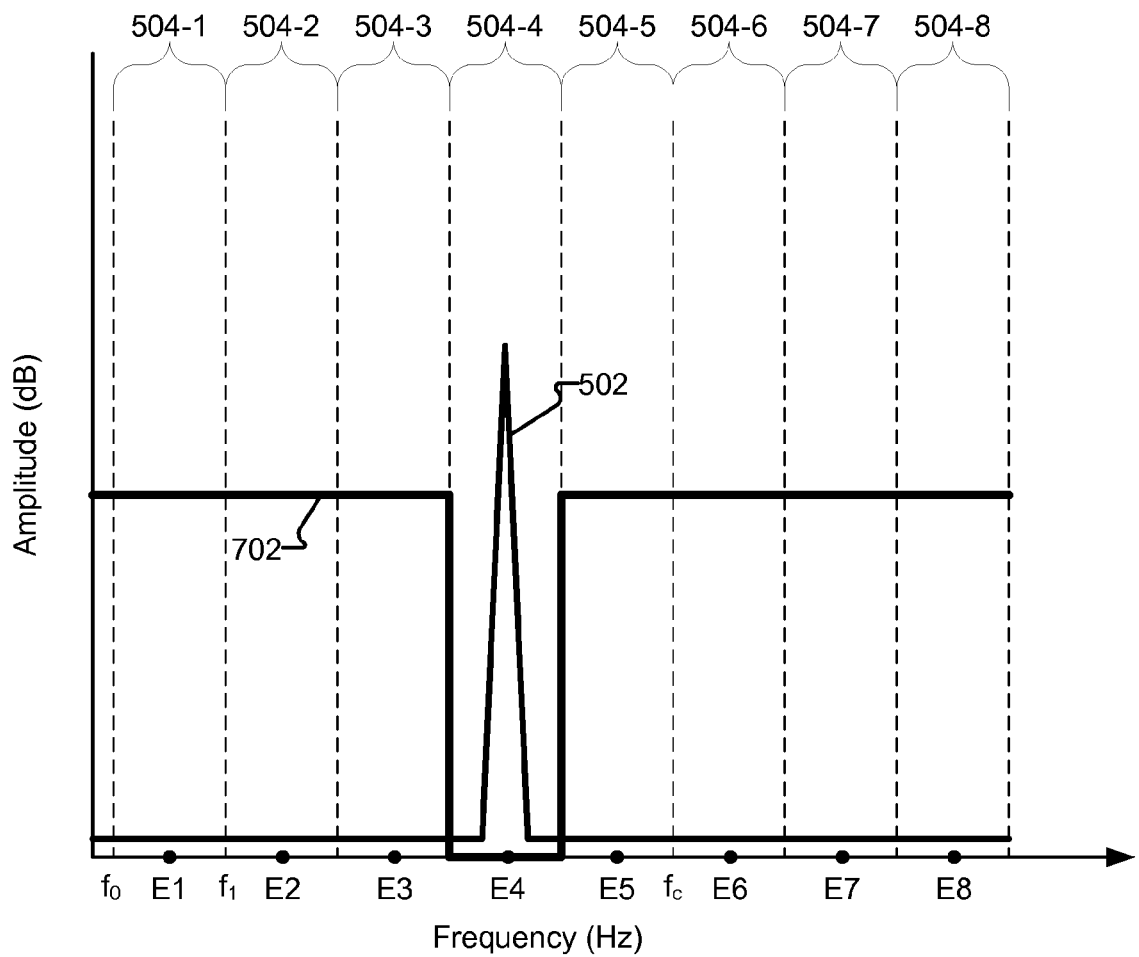
FIG. 7 shows a frequency domain representation of a tone and a masking signal that may be presented together according to principles described herein.

To illustrate, FIG. 7 shows a frequency domain representation of tone 502 and a masking signal 702 that may be presented together (i.e., concurrently) to the auditory prosthesis patient. As shown, tone 502 still has the same frequency that it did in the example of FIG. 5.

Masking signal 702 is configured to mask frequencies not included within frequency band 504-4. As shown, masking signal 702 may be notched in that it does not mask frequencies (e.g., the frequency of tone 502) included within frequency band 504-4. It will be recognized that masking signal 702 may include any suitable content (e.g., notched noise, asynchronous noise, etc.) as may serve a particular implementation.

While the tone (e.g., tone 502) is being applied in the presence of the masking signal (e.g., masking signal 702) during the second time period, processing facility 404 may use the same electrode used to record the first evoked response to monitor for and record a second evoked response that occurs in response to the concurrent presentation of the tone and masking signal.

Once the first and second evoked responses are both recorded, processing facility 404 may use the recorded first and second evoked response to determine whether the intracochlear region associated with the frequency band that includes the frequency of the tone is a dead region. For example, processing facility 404 may compare the first and second evoked responses to determine whether the second evoked response is within a predetermined range of the first evoked response. If the second evoked response is within the predetermined range of the first evoked response, processing facility 404 may determine that the intracochlear region is not a dead region. However, if the second evoked response is not within the predetermined range of the first evoked response, processing facility 404 may determine that the intracochlear region is a dead region.

Figure 8:
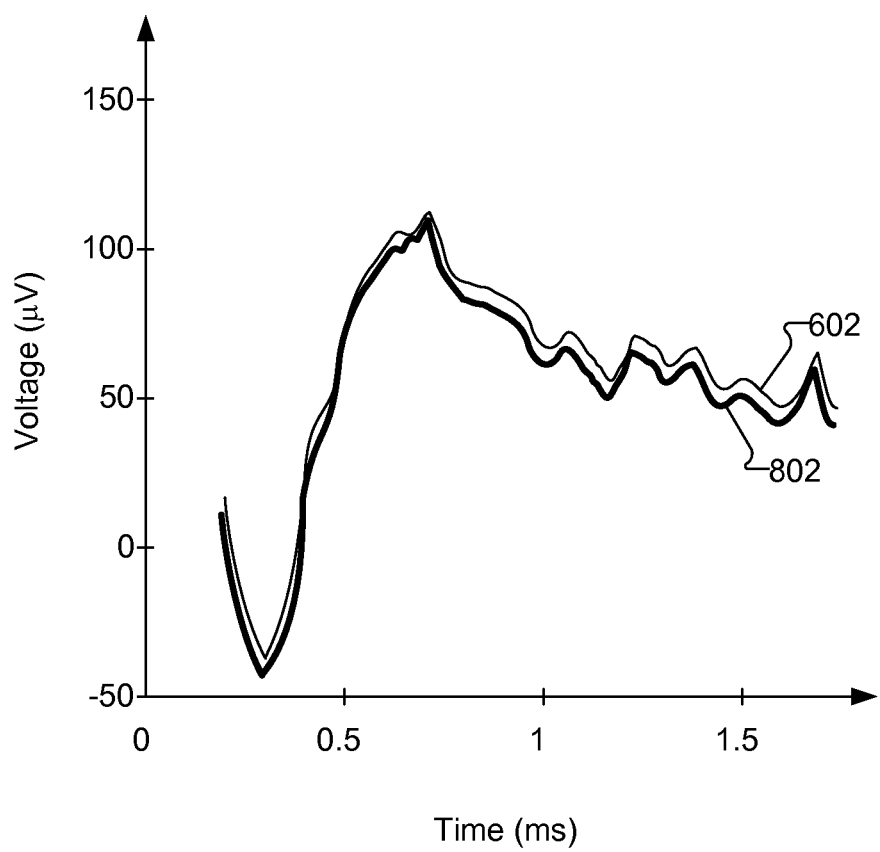
FIG. 8 illustrates an exemplary evoked response according to principles described herein.

For example, FIG. 8 illustrates an exemplary evoked response 802 that may occur in response to a presentation of tone 502 in the presence of masking signal 702. For the sake of comparison, FIG. 8 also shows the evoked response 602 described in connection with FIG. 6 and that may occur in response to a presentation of tone 502 in isolation.

As shown, evoked response 802 is similar (e.g., in shape and amplitude) to evoked response 602. In this case, processing facility 404 may determine that evoked response 802 is within a predetermined range of evoked response 602. The predetermined range may be amplitude-based and/or based on any other factor as may serve a particular implementation and may be set by a user (e.g., a clinician).

In response to the determination that evoked response 802 is within the predetermined range of evoked response 602, processing facility 404 may determine that the intracochlear region associated with frequency band 504-4 is not dead.

The basis for this determination lies in the fact that if a particular intracochlear region is not dead, the hair cells and/or neurons in that region are primarily responsible for the evoked response detected by the electrode (e.g., electrode E4 shown in FIG. 5). In contrast, if the particular intracochlear region is dead, hair cells and/or neurons outside that region (e.g., in intracochlear regions that surround the intracochlear region) are primarily responsible for the evoked response detected by the electrode (e.g., electrode E4 shown in FIG. 5).

In light of this, when tone 502 is presented to the patient, components of tone 502 may spread (due to physiological properties of the intracochlear space) to intracochlear regions that surround the intracochlear region associated with frequency band 504-4. Hence, hair cells and/or neurons in the surrounding intracochlear regions may respond to tone 502 and contribute to the evoked response recorded by electrode E4. If the intracochlear region associated with frequency band 504-4 is not dead, the contribution of the hair cells and/or neurons in the surrounding intracochlear regions to the evoked response recorded by electrode E4 is negligible compared to that of the hair cells and/or neurons included in the intracochlear region associated with frequency band 504-4. However, if the intracochlear region associated with frequency band 504-4 is dead, the hair cells and/or neurons in the surrounding intracochlear regions are primarily responsible for the evoked response recorded by electrode E4.

Hence, if the intracochlear region associated with frequency band 504-4 is not dead, the evoked response recorded by electrode E4 when tone 502 is presented in the presence of masking signal 702 will not differ significantly from the evoked response recorded by electrode E4 when tone 502 is presented in isolation because the hair cells and/or neurons in the intracochlear region associated with frequency band 504-4 are primarily responsible for both evoked responses.

Figure 9:
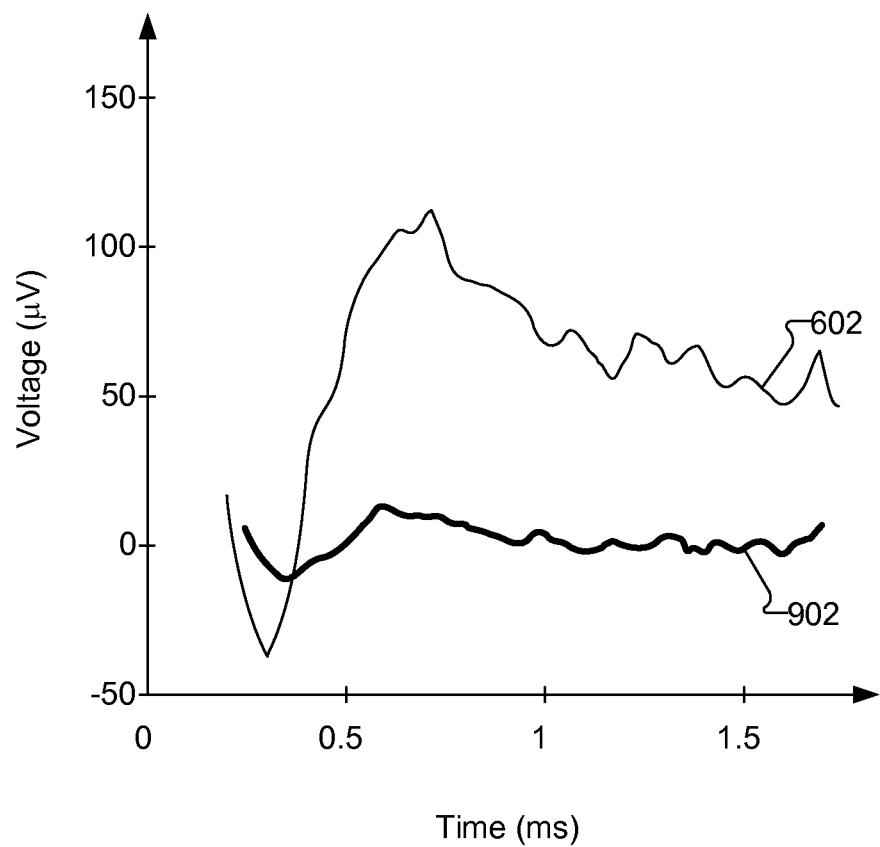
FIG. 9 illustrates another exemplary evoked response according to principles described herein.

In contrast, if the intracochlear region associated with frequency band 504-4 is dead, the evoked responses will differ because the components of tone 502 that have spread into surrounding intracochlear regions are masked by masking signal 702. For example, FIG. 9 illustrates another exemplary evoked response 902 that may occur in response to a presentation of tone 502 in the presence of masking signal 702 and that may differ significantly (e.g., in terms of amplitude and/or shape) than evoked response 602 that may occur in response to a presentation of tone 502 in isolation. In this case, processing facility 404 may determine that evoked response 902 is not within the predetermined range of evoked response 602 and thereby determine that the intracochlear region associated with frequency band 504-4 is dead.

Processing facility 404 may perform one or more predetermined actions in accordance with the determination whether the intracochlear region is dead. For example, the patient may be fitted with an EAS system similar to that described in connection with FIG. 3. In this scenario, processing facility 404 may set one or more control parameters governing an operation of the EAS system in accordance with the determination whether the intracochlear region is dead. For example, if processing facility 404 determines that the intracochlear region is not dead, processing facility 404 may direct the EAS system to amplify acoustic stimulation used by the EAS system to represent audio signals that are presented to the patient and that have frequencies included in the frequency band associated with the intracochlear region. The degree of amplification to be used for the acoustic stimulation may be based on a comparison of the first and second evoked responses.

To illustrate, processing facility 404 may determine that the intracochlear region associated with frequency band 504-4 is not dead. However, the first and second evoked responses may differ in amplitude (e.g., if the intracochlear region has a relatively few number of functioning hair cells and/or neurons). In this case, processing facility 404 may determine that acoustic stimulation used by the EAS system to represent audio signals that have frequencies included in frequency band 504-4 should be amplified to a degree to compensate for the relatively few number of functioning hair cells and/or neurons. Processing facility 404 may direct the EAS system to amplify the acoustic stimulation in any suitable manner.

In contrast, if processing facility 404 determines that the intracochlear region associated with frequency band 504-4 is dead, processing facility 404 may direct the EAS system to not amplify acoustic stimulation to represent audio signals that have frequencies included in frequency band 504-4. In some cases processing facility 404 may direct EAS system to not use acoustic stimulation at all to represent audio signals that have frequencies included in frequency band 504-4. In these cases, processing facility 404 may direct the EAS system to use electrical stimulation in place of acoustic stimulation to represent audio signals that have frequencies included in frequency band 504-4.

It will be recognized that intracochlear regions may have different numbers of functioning hair cells and/or neurons. Hence, some intracochlear regions may be more healthy than others. In some examples, diagnostic system 400 may assess a relative health of an intracochlear region and take one or more actions based on the relative heath of the intracochlear region.

Figure 10:
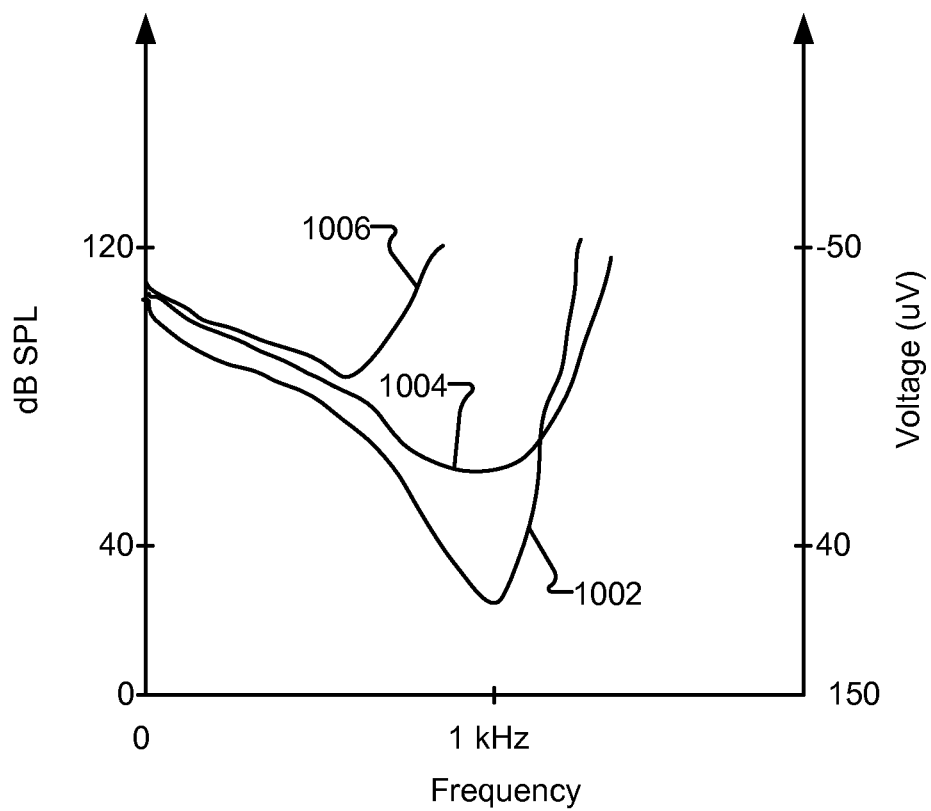
FIG. 10 illustrates various tuning curves according to principles described herein.

To illustrate, diagnostic system 400 may vary the width of masking signal 702 (i.e., the width of the notch in masking signal 702 while applying tone 502) or the location of the notch in the noise. As this is done, diagnostic system 400 may measure evoked responses to generate a tuning curve associated with tone 502. To illustrate, FIG. 10 shows various tuning curves 1002, 1004, and 1006 that may be generated for tone 502. The y-axis on the left shows responses for threshold of tone 502. The y-axis on the right shows amplitudes for tuning curves made using the evoked responses.

Tuning curve 1002 shows a normal response for a 1000 Hz test acoustic tone. Tuning curve 1002 indicates that the corresponding intracochlear region is healthy. Hence, in this case, diagnostic system 400 may determine to provide information acoustically only, and perhaps even disable one or more apical electrodes so that their electrical stimulation does not interfere with the acoustic stimulation.

Tuning curve 1004 shows an abnormal response for the 1000 Hz test acoustic tone. Tuning curve 1004 indicates that the intracochlear region is not completely healthy, but not completely dead either. In this case, diagnostic system 400 may determine to use an overlap of both acoustic and electrical stimulation to represent sounds in this intracochlear region.

Tuning curve 1006 shows a dead response for the 1000 Hz test acoustic tone. Tuning curve 1006 indicates that the intracochlear region is dead. In this case, diagnostic system 400 may determine to use electrical stimulation only to represent sounds in this intracochlear region.

Diagnostic system 400 (i.e., facilities 402-406) may be implemented by any suitable combination of components. For example, diagnostic system 400 may be entirely implemented by an EAS sound processor (e.g., sound processor 104 shown in FIG. 3). In this manner, the EAS sound processor may automatically identify and compensate for one or more intracochlear dead regions regardless of whether the patient is at a clinic participating in a fitting session.

Figure 11:
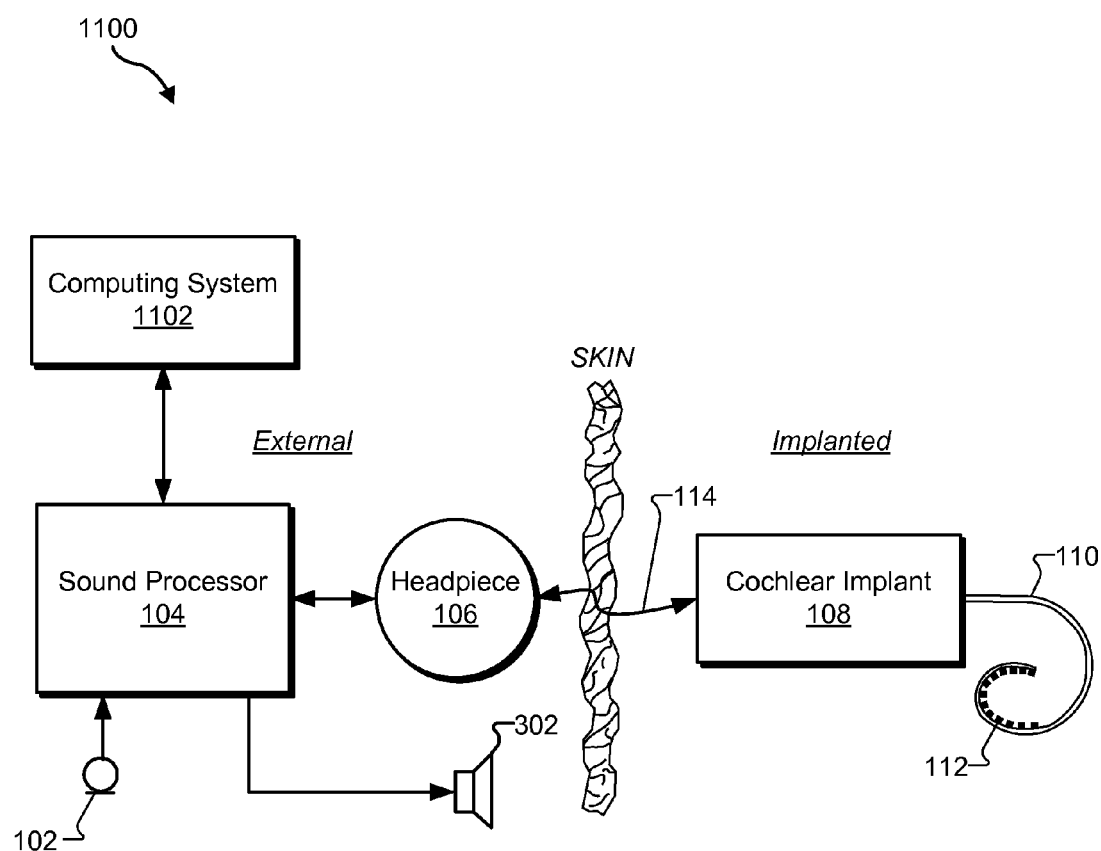
FIG. 11 shows an exemplary implementation of the diagnostic system of FIG. 4 according to principles described herein.

Additionally or alternatively, diagnostic system 400 may be at least partially implemented by a computing system that may be selectively and communicatively coupled to sound processor 104. To illustrate, FIG. 11 shows an exemplary configuration 1100 in which a computing system 1102 is communicatively coupled to sound processor 104. Computing system 1102 may be implemented by any suitable combination of computing and communication devices including, but not limited to, a fitting station, a personal computer, a laptop computer, a handheld device, a mobile device (e.g., a mobile phone), a clinician's programming interface ("CPI") device, and/or any other suitable component as may serve a particular implementation. In some examples, computing system 1102 may provide one or more graphical user interfaces ("GUIs") (e.g., by presenting the one or more GUIs by way of a display screen) with which a clinician or other user may interact.

Computing system 1102 may perform any of the functions performed by facilities 402-406. For example, computing system 1102 may present acoustic content (e.g., a tone in isolation and/or a tone in the presence of a masking signal) by directing sound processor 104 to present the acoustic content to the patient by way of receiver 302. Additionally or alternatively, sound processor 104 may transmit data representative of evoked responses to computing system 1102. Computing system 1102 may perform any suitable action (including any of the predetermined actions described herein) based on the data representative of the evoked responses. For example, computing system 1102 may compare the evoked responses and determine whether an intracochlear region is dead as described above. Additionally or alternatively, computing system 1102 may present a graph representative of the evoked responses by way of a display screen for analysis by a clinician or other user, provide one or more recommendations in accordance with the evoked responses (e.g., one or more recommendations with respect to setting one or more stimulation parameters that govern auditory prosthesis system 100), and/or perform any other suitable action as may serve a particular implementation.

Figure 12:
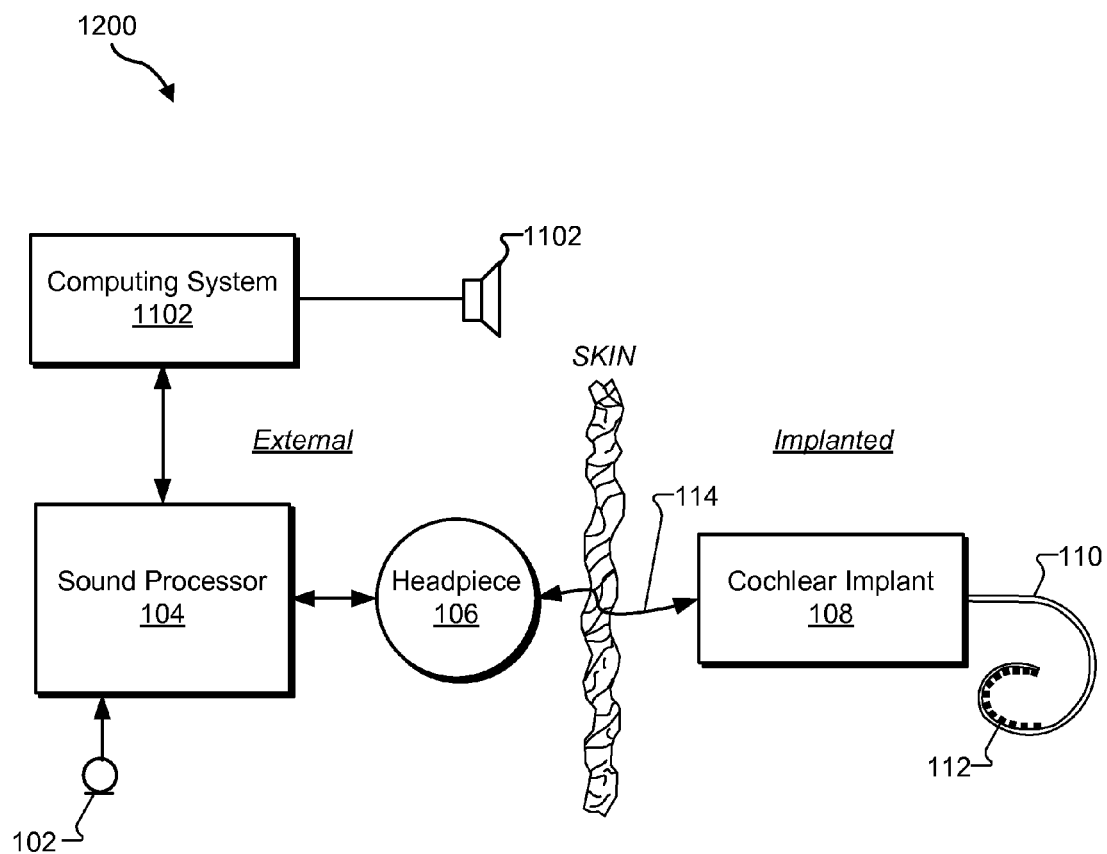
FIG. 12 shows another exemplary implementation of the diagnostic system of FIG. 4 according to principles described herein.

In some examples, computing system 1102 may entirely implement diagnostic system 400. For example, FIG. 12 shows an exemplary configuration 1200 in which a receiver 1202 is coupled directly to computing system 1102. Configuration 1200 may be used in scenarios in which the patient is fitted with an auditory prosthesis system 100 that does not include a receiver (e.g., the cochlear implant system shown in FIG. 1). For example, configuration 1200 may be used to determine whether a cochlear implant patient is a candidate for an EAS system.

Figure 13:
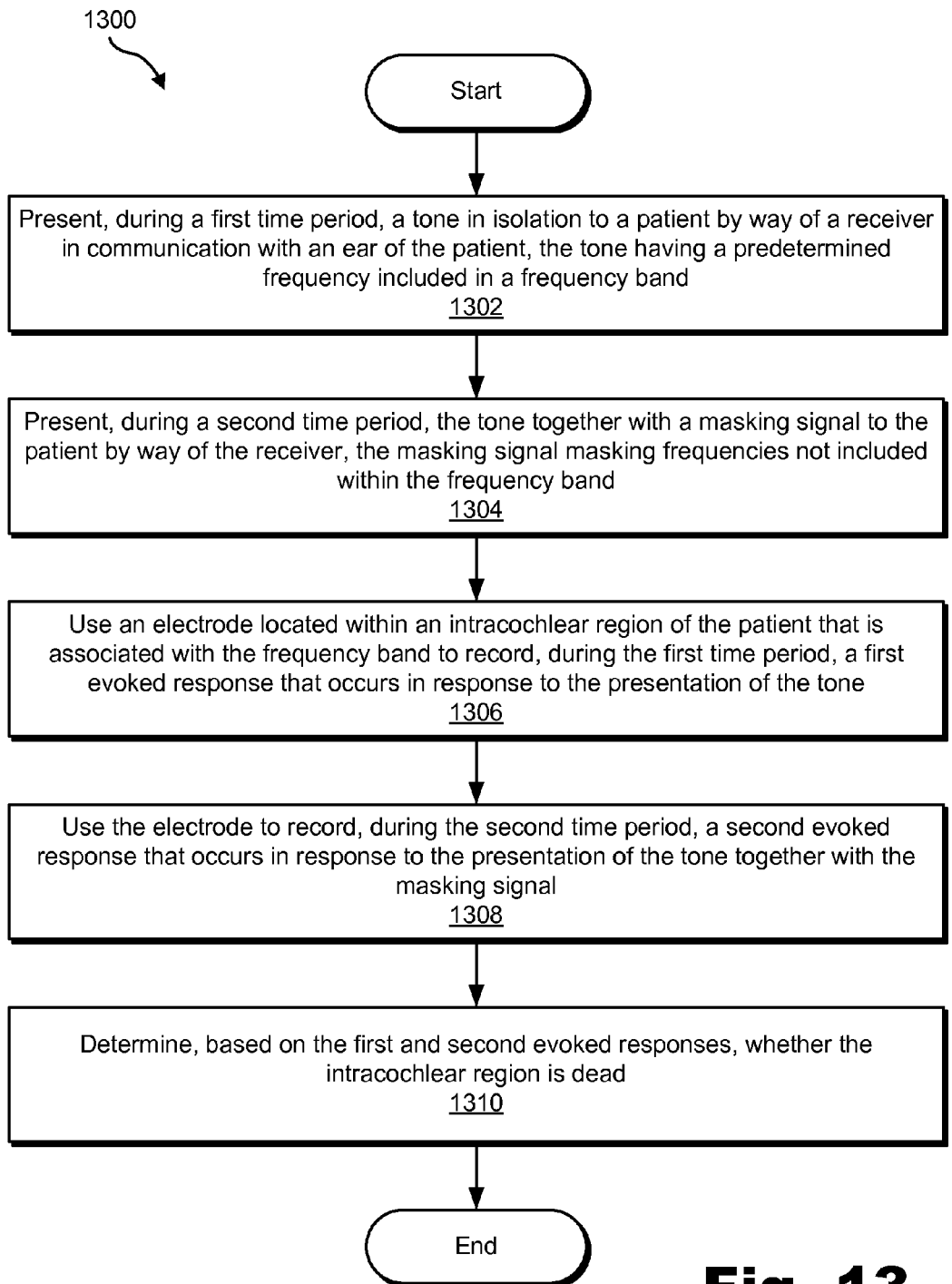
FIG. 13 illustrates an exemplary method of identifying one or more intracochlear dead regions according to principles described herein.

FIG. 13 illustrates an exemplary method 1300 of identifying one or more intracochlear dead regions. While FIG. 13 illustrates exemplary steps according to one embodiment, other embodiments may omit, add to, reorder, and/or modify any of the steps shown in FIG. 13. One or more of the steps shown in FIG. 13 may be performed by diagnostic system 400 and/or any implementation thereof.

In step 1302, a diagnostic system presents, during a first time period, a tone in isolation to a patient by way of a receiver in communication with an ear of the patient, the tone having a predetermined frequency included in a frequency band. Step 1302 may be performed in any of the ways described herein.

In step 1304, the diagnostic system presents, during a second time period, the tone together with a masking signal to the patient by way of the receiver, the masking signal masking frequencies not included within the frequency band. Step 1304 may be performed in any of the ways described herein.

In step 1306, the diagnostic system uses an electrode located within an intracochlear region of the patient that is associated with the frequency band to record, during the first time period, a first evoked response that occurs in response to the presentation of the tone. Step 1306 may be performed in any of the ways described herein.

In step 1308, the diagnostic system uses the electrode to record, during the second time period, a second evoked response that occurs in response to the presentation of the tone together with the masking signal. Step 1308 may be performed in any of the ways described herein.

In step 1310, the diagnostic system determines, based on the first and second evoked responses, whether the intracochlear region is dead. Step 1310 may be performed in any of the ways described herein.

In certain embodiments, one or more of the processes described herein may be implemented at least in part as instructions embodied in a non-transitory computer-readable medium and executable by one or more computing devices. In general, a processor (e.g., a microprocessor) receives instructions, from a non-transitory computer-readable medium, (e.g., a memory, etc.), and executes those instructions, thereby performing one or more processes, including one or more of the processes described herein. Such instructions may be stored and/or transmitted using any of a variety of known computer-readable media.

A computer-readable medium (also referred to as a processor-readable medium) includes any non-transitory medium that participates in providing data (e.g., instructions) that may be read by a computer (e.g., by a processor of a computer). Such a medium may take many forms, including, but not limited to, non-volatile media, and/or volatile media. Non-volatile media may include, for example, optical or magnetic disks and other persistent memory. Volatile media may include, for example, dynamic random access memory ("DRAM"), which typically constitutes a main memory. Common forms of computer-readable media include, for example, a disk, hard disk, magnetic tape, any other magnetic medium, a CD-ROM, DVD, any other optical medium, a RAM, a PROM, an EPROM, a FLASH-EEPROM, any other memory chip or cartridge, or any other tangible medium from which a computer can read.

Figure 14:
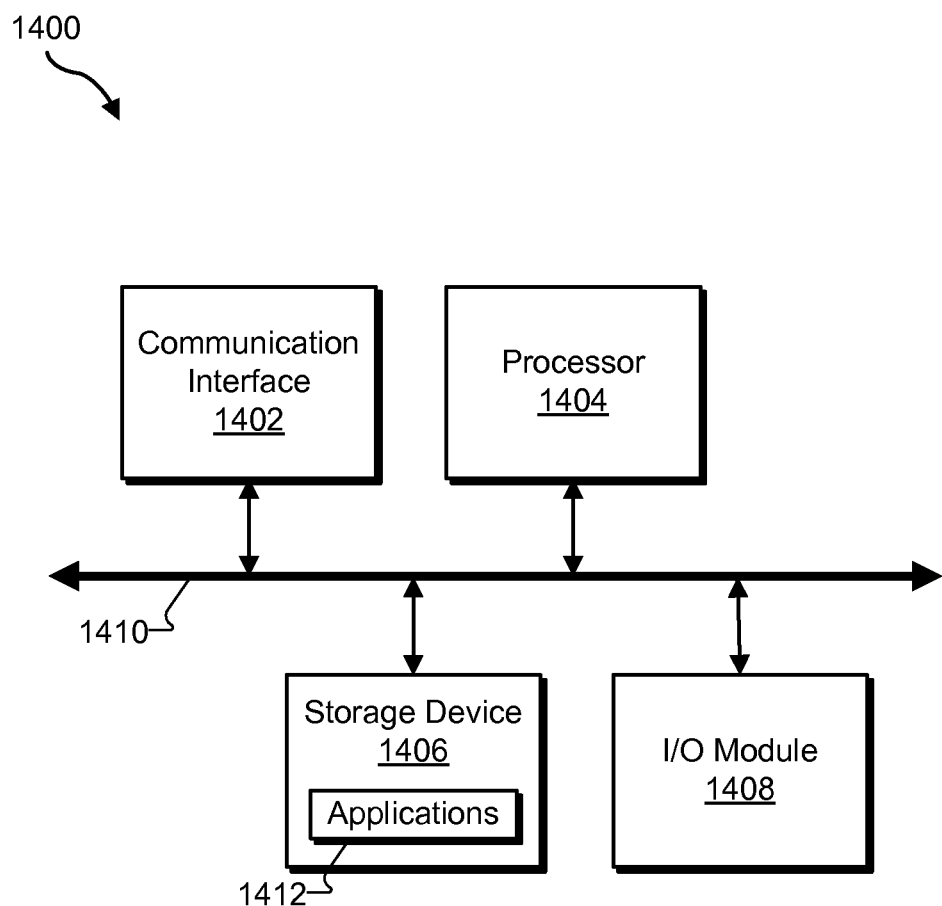
FIG. 14 illustrates an exemplary computing device according to principles described herein.

FIG. 14 illustrates an exemplary computing device 1400 that may be configured to perform one or more of the processes described herein. As shown in FIG. 14, computing device 1400 may include a communication interface 1402, a processor 1404, a storage device 1406, and an input/output ("I/O") module 1408 communicatively connected via a communication infrastructure 1410. While an exemplary computing device 1400 is shown in FIG. 14, the components illustrated in FIG. 14 are not intended to be limiting. Additional or alternative components may be used in other embodiments. Components of computing device 1400 shown in FIG. 14 will now be described in additional detail.

Communication interface 1402 may be configured to communicate with one or more computing devices. Examples of communication interface 1402 include, without limitation, a wired network interface (such as a network interface card), a wireless network interface (such as a wireless network interface card), a modem, an audio/video connection, and any other suitable interface.

Processor 1404 generally represents any type or form of processing unit capable of processing data or interpreting, executing, and/or directing execution of one or more of the instructions, processes, and/or operations described herein. Processor 1404 may direct execution of operations in accordance with one or more applications 1412 or other computer-executable instructions such as may be stored in storage device 1406 or another computer-readable medium.

Storage device 1406 may include one or more data storage media, devices, or configurations and may employ any type, form, and combination of data storage media and/or device. For example, storage device 1406 may include, but is not limited to, a hard drive, network drive, flash drive, magnetic disc, optical disc, random access memory ("RAM"), dynamic RAM ("DRAM"), other non-volatile and/or volatile data storage units, or a combination or sub-combination thereof. Electronic data, including data described herein, may be temporarily and/or permanently stored in storage device 1406. For example, data representative of one or more executable applications 1412 configured to direct processor 1404 to perform any of the operations described herein may be stored within storage device 1406. In some examples, data may be arranged in one or more databases residing within storage device 1406.

I/O module 1408 may be configured to receive user input and provide user output and may include any hardware, firmware, software, or combination thereof supportive of input and output capabilities. For example, I/O module 1408 may include hardware and/or software for capturing user input, including, but not limited to, a keyboard or keypad, a touch screen component (e.g., touch screen display), a receiver (e.g., an RF or infrared receiver), and/or one or more input buttons.

I/O module 1408 may include one or more devices for presenting output to a user, including, but not limited to, a graphics engine, a display (e.g., a display screen, one or more output drivers (e.g., display drivers), one or more audio speakers, and one or more audio drivers. In certain embodiments, I/O module 1408 is configured to provide graphical data to a display for presentation to a user. The graphical data may be representative of one or more graphical user interfaces and/or any other graphical content as may serve a particular implementation.

In some examples, any of the facilities and/or systems described herein may be implemented by or within one or more components of computing device 1400. For example, one or more applications 1412 residing within storage device 1406 may be configured to direct processor 1404 to perform one or more processes or functions associated with any of the facilities and/or systems described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
an acoustic stimulation management facility that
presents, during a first time period, a tone in isolation to a patient by way of a receiver in communication with an ear of the patient, the tone having a predetermined frequency included in a frequency band, and
presents, during a second time period, the tone together with a masking signal to the patient by way of the receiver, the masking signal masking frequencies not included within the frequency band; and
a processing facility communicatively coupled to the acoustic stimulation management facility and that
uses an electrode located within an intracochlear region of the patient that is associated with the frequency band to
record, during the first time period, a first evoked response that occurs in response to the presentation of the tone, and
record, during the second time period, a second evoked response that occurs in response to the presentation of the tone together with the masking signal, and
determines, based on the first and second evoked responses, whether the intracochlear region is dead.

2. The system of claim 1, wherein the processing facility determines whether the intracochlear region is dead by comparing the first and second evoked responses.

3. The system of claim 1, wherein the processing facility:
determines that the intracochlear region is not dead if the second evoked response is within a predetermined range of the first evoked response; and
determines that the intracochlear region is dead if the second evoked response is not within the predetermined range of the first evoked response.

4. The system of claim 1, wherein the processing facility sets one or more control parameters governing an operation of an electro-acoustic stimulation ("EAS") system associated with the patient in accordance with the determination whether the intracochlear region is dead.

5. The system of claim 4, wherein, if the processing facility determines that the intracochlear region is not dead, the processing facility sets the one or more control parameters by directing the EAS system to amplify acoustic stimulation used by the EAS system to represent audio signals that are presented to the patient and that have frequencies included in the frequency band.

6. The system of claim 5, wherein the processing facility determines a degree of amplification to be used for the acoustic stimulation based on a comparison of the first and second evoked responses.

7. The system of claim 4, wherein, if the processing facility determines that the intracochlear region is dead, the processing facility sets the one or more control parameters by directing the EAS system to not amplify acoustic stimulation used by the EAS system to represent audio signals that are presented to the patient and that have frequencies included in the frequency band.

8. The system of claim 4, wherein, if the processing facility determines that the intracochlear region is dead, the processing facility sets the one or more control parameters by directing the EAS system to use electrical stimulation to represent audio signals that are presented to the patient and that have frequencies included in the frequency band.

9. The system of claim 1, wherein the processing facility:
determines that the intracochlear region is not dead;
determines a relative health of the intracochlear region; and
sets one or more control parameters governing an operation of an electro-acoustic stimulation ("EAS") system associated with the patient in accordance with the determination of the relative health of the intracochlear region.

10. The system of claim 1, wherein the processing facility is implemented by a computing system separate from and communicatively coupled to an auditory prosthesis system associated with the patient.

11. The system of claim 1, wherein the acoustic stimulation management facility and the processing facility are implemented by an electro-acoustic stimulation system associated with the patient.

12. A system comprising:
an electro-acoustic stimulation ("EAS") sound processor configured to be located external to a patient;
a cochlear implant communicatively coupled to the EAS sound processor and configured to be implanted within the patient;
an electrode array communicatively coupled to the cochlear implant and configured to be located within a cochlea of the patient; and
a receiver communicatively coupled to the EAS sound processor and configured to be in communication with an ear of the patient;
wherein the EAS sound processor
presents, during a first time period, a tone in isolation to the patient by way of the receiver, the tone having a predetermined frequency included in a frequency band,
presents, during a second time period, the tone together with a masking signal to the patient by way of the receiver, the masking signal masking frequencies not included within the frequency band,
uses an electrode included in the electrode array and located within an intracochlear region that is associated with the frequency band to
record, during the first time period, a first evoked response that occurs in response to the presentation of the tone, and
record, during the second time period, a second evoked response that occurs in response to the presentation of the tone together with the masking signal, and
determines, based on the first and second evoked responses, whether the intracochlear region is dead.

13. The system of claim 12, wherein the EAS sound processor uses the electrode to record the first and second evoked responses by directing the cochlear implant to use the electrode to record the first and second evoked responses.

14. The system of claim 12, wherein the EAS sound processor determines whether the intracochlear region is dead by comparing the first and second evoked responses.

15. The system of claim 12, wherein the EAS sound processor:
    determines that the intracochlear region is not dead if the second evoked response is within a predetermined range of the first evoked response; and
    determines that the intracochlear region is dead if the second evoked response is not within the predetermined range of the first evoked response.

16. The system of claim 12, wherein the EAS sound processor sets one or more control parameters governing an operation of at least one of the EAS sound processor and the cochlear implant in accordance with the determination whether the intracochlear region is dead.

17. A system comprising:
    an acoustic stimulation management facility that presents acoustic content by way of a receiver in communication with an ear of the patient, the audio signal having a predetermined frequency included in a frequency band; and
    a processing facility communicatively coupled to the acoustic stimulation management facility and that uses an electrode located within an intracochlear region of the patient that is associated with the frequency band to record at least one of a cochlear microphonics response and a summating potential.

18. A method comprising:
    presenting, by a diagnostic system during a first time period, a tone in isolation to a patient by way of a receiver in communication with an ear of the patient, the tone having a predetermined frequency included in a frequency band;
    presenting, by the diagnostic system during a second time period, the tone together with a masking signal to the patient by way of the receiver, the masking signal masking frequencies not included within the frequency band;
    using, by the diagnostic system, an electrode located within an intracochlear region of the patient that is associated with the frequency band to
        record, during the first time period, a first evoked response that occurs in response to the presentation of the tone, and
        record, during the second time period, a second evoked response that occurs in response to the presentation of the tone together with the masking signal; and
    determining, by the diagnostic system, based on the first and second evoked responses, whether the intracochlear region is dead.

19. The method of claim 17, wherein the determining comprises:
    determining that the intracochlear region is not dead if the second evoked response is within a predetermined range of the first evoked response; and
    determining that the intracochlear region is dead if the second evoked response is not within the predetermined range of the first evoked response.

20. The method of claim 17, further comprising setting, by the diagnostic system, one or more control parameters governing an operation of at least one of the EAS sound processor and the cochlear implant in accordance with the determination whether the intracochlear region is dead.

* * * * *